(12) United States Patent
Carrubba

(10) Patent No.: US 9,757,270 B2
(45) Date of Patent: Sep. 12, 2017

(54) OSTOMY APPLIANCE

(71) Applicant: Georgann M. Carrubba, Batavia, NY (US)

(72) Inventor: Georgann M. Carrubba, Batavia, NY (US)

(73) Assignee: TENCAR INC., Batavia, NY (US)

( * ) Notice: Subject to any disclaimer, the term of this patent is extended or adjusted under 35 U.S.C. 154(b) by 248 days.

(21) Appl. No.: 14/617,460

(22) Filed: Feb. 9, 2015

(65) Prior Publication Data

US 2016/0228284 A1 Aug. 11, 2016

(51) Int. Cl.
*A61F 5/448* (2006.01)

(52) U.S. Cl.
CPC .................... *A61F 5/448* (2013.01)

(58) Field of Classification Search
CPC combination set(s) only.
See application file for complete search history.

(56) References Cited

U.S. PATENT DOCUMENTS

| | | | |
|---|---|---|---|
| 2,341,984 A * | 2/1944 | Graves | A61F 5/445 604/332 |
| 2,639,710 A | 5/1953 | Fazio | |
| 2,708,802 A | 5/1955 | Baker et al. | |
| 3,690,320 A | 9/1972 | Riely | |
| 3,736,934 A | 6/1973 | Hennessy | |
| 3,825,005 A | 7/1974 | Fenton | |
| 4,219,023 A | 8/1980 | Galindo | |
| 4,294,252 A | 10/1981 | Einset | |
| 4,439,191 A | 3/1984 | Hogan | |
| 4,460,363 A | 7/1984 | Steer et al. | |
| 4,519,797 A | 5/1985 | Hall | |
| 4,543,097 A | 9/1985 | Van Polen | |
| 4,636,206 A * | 1/1987 | Ederati | A61F 5/44 604/340 |
| 4,723,951 A | 2/1988 | Steer | |
| 4,784,656 A | 11/1988 | Christian | |
| 4,846,798 A | 7/1989 | Holtermann et al. | |
| 4,950,223 A * | 8/1990 | Silvanov | A61F 5/441 128/DIG. 25 |
| 5,098,420 A | 3/1992 | Iacone | |
| 5,178,615 A | 1/1993 | Steer et al. | |
| 5,209,744 A | 5/1993 | Abe et al. | |
| 5,248,308 A | 9/1993 | von Emster | |
| 5,312,381 A | 5/1994 | Brooks | |
| 5,330,454 A * | 7/1994 | Klingler | A61F 5/448 604/338 |

(Continued)

FOREIGN PATENT DOCUMENTS

| | | |
|---|---|---|
| CN | 201840569 | 5/2011 |
| DK | 177034 B1 | 2/2011 |

(Continued)

*Primary Examiner* — Tatyana Zalukaeva
*Assistant Examiner* — Guy K Townsend
(74) *Attorney, Agent, or Firm* — Woods Oviatt Gilman LLP; Katherine H. McGuire, Esq.

(57) ABSTRACT

An ostomy appliance having a releasable receptacle for concealing an ostomy bag where the receptacle is asymmetrical and includes an enlarged cavity portion located below the stoma which provides additional area into which the bag may unroll as waste collects therein. In an alternate embodiment there is no bag and waste collects directly into the receptacle.

15 Claims, 4 Drawing Sheets

(56) References Cited

U.S. PATENT DOCUMENTS

| | | |
|---|---|---|
| 5,470,325 A | 11/1995 | Fundock |
| 5,520,670 A | 5/1996 | Blum |
| 5,617,616 A | 4/1997 | Cutts, Sr. |
| 5,626,569 A | 5/1997 | Holtermann et al. |
| 5,759,180 A | 6/1998 | Myhres |
| 5,785,695 A | 7/1998 | Sato et al. |
| 5,843,054 A | 12/1998 | Honig |
| 5,968,024 A | 10/1999 | Freeman |
| 6,050,982 A | 4/2000 | Wheeler |
| D452,374 S | 12/2001 | Kim |
| 6,415,947 B1 | 7/2002 | Kim |
| 6,679,866 B1 | 1/2004 | Gunawan |
| D488,031 S | 4/2004 | Kim |
| 6,723,079 B2 * | 4/2004 | Cline ................. A61F 5/448 128/887 |
| 6,764,473 B2 | 7/2004 | Morton |
| 6,793,096 B1 | 9/2004 | Seok |
| D499,931 S | 12/2004 | Kim |
| 7,722,586 B2 | 5/2010 | Mullejans et al. |
| 7,857,796 B2 | 12/2010 | Cline et al. |
| 7,931,631 B2 | 4/2011 | Pedersen et al. |
| 8,657,799 B2 * | 2/2014 | Carrubba ............ A61F 5/448 604/318 |
| 8,740,865 B2 | 6/2014 | Krystek et al. |
| 9,345,612 B2 * | 5/2016 | Hanuka ............... A61F 5/4401 |
| 9,517,157 B2 * | 12/2016 | Hanuka ............... A61F 5/4401 |
| 2004/0073179 A1 * | 4/2004 | Andersen ............ A61F 5/445 604/338 |
| 2005/0113770 A1 | 5/2005 | Pedersen et al. |
| 2005/0256466 A1 | 11/2005 | Winkler |
| 2006/0154054 A1 | 7/2006 | Banks et al. |
| 2006/0258997 A1 | 11/2006 | Belt |
| 2007/0129695 A1 * | 6/2007 | Blum ................. A61F 5/445 604/338 |
| 2008/0269698 A1 * | 10/2008 | Alexander .......... A61F 5/445 604/332 |
| 2008/0294129 A1 | 11/2008 | Giori et al. |
| 2009/0234312 A1 | 9/2009 | O'Toole et al. |
| 2011/0106032 A1 * | 5/2011 | Kratky ................ A61F 5/448 604/337 |
| 2012/0109086 A1 * | 5/2012 | Tsai .................... A61F 5/448 604/335 |
| 2012/0179124 A1 * | 7/2012 | Nguyen-Demary .... A61F 5/448 604/333 |
| 2013/0116636 A1 * | 5/2013 | Carrubba ............ A61F 5/445 604/318 |
| 2013/0304008 A1 * | 11/2013 | Hanuka .............. A61F 5/4401 604/334 |
| 2014/0148771 A1 * | 5/2014 | Luce .................. A61F 5/445 604/345 |
| 2014/0249494 A1 * | 9/2014 | Bird .................... A61F 5/445 604/344 |
| 2014/0276500 A1 * | 9/2014 | Scott .................. A61F 5/449 604/343 |

FOREIGN PATENT DOCUMENTS

| | | |
|---|---|---|
| EP | 1129680 | 9/2001 |
| EP | 1 348 411 A1 | 1/2003 |
| EP | 1 985 267 A1 | 10/2008 |
| KR | 10-0983870 | 9/2010 |
| WO | 03/026541 | 4/2003 |
| WO | 2010/060115 | 5/2010 |
| WO | 2011/031822 A1 | 3/2011 |

* cited by examiner

OSTOMY APPLIANCE

BACKGROUND OF THE INVENTION

The present invention relates to ostomy appliances. More particularly, the present invention relates to an ostomy appliance which is designed to provide a high level of discreteness to the user on an as needed basis.

An "ostomy" is the generic term for a surgical procedure such as the ileostomy, colostomy and urostomy which leave the patient with a digestive waste opening formed by attaching the patient's intestine (small intestine in the case of an ileostomy; large intestine in the case of a colostomy) to the perimeter of an incision made in the abdominal wall. This part of the intestine is surgically opened to form what is called the "stoma" wherethrough digestive waste exits the body. The procedure may be reversible or irreversible depending on the circumstances. It is estimated that up to 750,000 Americans have an ostomy.

A digestive waste collection bag is attached about the stoma to collect the waste existing therefrom. The collection bag and associated body attachment parts are commonly referred to as the ostomy appliance or assembly. Ostomy appliances are offered in single piece and two piece systems. In the single piece system, the bag has an opening which is aligned with an opening in and then permanently fixed to a disc or flange which has an adhesive surface opposite the bag which secures the flange and bag to the body about the stoma. In the two-piece system, the bag is detachably secured to the flange, commonly via a snap ring on the flange which fits into a cooperatively formed groove attached to the perimeter of the bag opening. In either the single or two piece systems, the bag typically includes an open end opposite the flange end which may be alternately open and closed using a clamp. The bag is clamped closed during use and opened to empty the waste contents from the bag. The bag may be cleaned and reused or discarded with a new bag being attached to the flange.

Users of ostomy appliances often complain about the inconveniences of the appliance including lack of discreteness. For example, there is no control over when waste deposits into the bag which may thus fill and noticeably expand beneath the clothing at inconvenient times, inevitably causing embarrassment to the user. Attempts to address this problem have been at best a minor improvement while others appear to pose the threat of actual physical harm to the user by applying a positive pressure against the stoma.

One example of an ostomy appliance which addresses the above drawbacks in the prior art is shown and described in commonly owned U.S. Pat. No. 8,657,799, the disclosure of which is incorporated herein by reference. The '799 patent provides an ostomy appliance which is compact and has a receptacle portion which accommodates a certain amount of waste before it must be opened and emptied. For users that desire to wear the ostomy appliance a bit longer than the '799 receptacle may allow, there remains a need for an ostomy appliance having a receptacle designed to accommodate a bit more waste. This would allow the user to wear the appliance for a longer time prior to opening and emptying yet still provide enhanced discreteness during periods of physical activity and close personal encounters, all without application of potentially dangerous pressures on the stoma as occurs in the prior art.

SUMMARY OF THE INVENTION

The present invention provides an ostomy appliance and method which includes a cup-shaped receptacle having an attachment mechanism about the open perimeter thereof which may be removably secured to a mating attachment mechanism (e.g., an ostomy flange) secured to the adhesive patch which includes a central opening for locating about the stoma opening on the user's body. The bag includes a ring element at the open stoma-facing end thereof which removably attaches to a mating ring element located around the stoma opening and radially inwardly of the receptacle attachment mechanism on the patch. When it is desired to contain the bag for increased discreteness, the user gathers or rolls the empty bag up upon itself into a rolled position, positions the receptacle over the bag and then secures the cooperative attachment mechanism together thereby securing the receptacle to the ostomy flange with the bag enclosed therein in the rolled condition.

The receptacle may have one or more vent holes formed therein to allow gas to escape therefrom. A vent cap may be provided which is normally closed but will automatically open upon a rise in pressure inside the receptacle to allow the egress of gas from the receptacle. Once the pressure is relieved the vent cap automatically closes. A covering may be placed over the receptacle to provide further discreteness and comfort to the user.

The receptacle includes an enlarged internal cavity which, when attached to the ostomy flange on the user's body, preferably extends downwardly in line with the length of the body toward the user's feet. This enlarged cavity portion of the receptacle provides portion within which the bag may deploy (e.g., unroll) as the bag fills with the user's waste. This particular embodiment thus allows the receptacle to remain in place for a longer time than a receptacle that has a smaller receptacle cavity size. In a preferred embodiment, the receptacle is asymmetrically shaped with the smaller side of the receptacle located above the stoma. This asymmetrical shape helps minimize the size of the receptacle while still proving added cavity portion where it is most useful. More particularly, the side of the receptacle which is smaller extends above the stoma where waste is not normally directed and the enlarged area is located on the opposite side of the receptacle where the waste and bag are directed by gravity when the user is sitting upright or standing.

When the bag is held in the receptacle, waste will deposit therein the usual manner. As waste enters the bag, the bag will begin to expand and unroll slightly within the confines of the receptacle. There is thus no positive pressure being applied to the stoma and waste is allowed to naturally exit the user's stoma and enter the bag. It is not intended that the receptacle be in place over the bag for more than a few hours at a time and it is therefore not expected that waste will be prevented from naturally exiting the stoma for any potentially harmful extended period of time. Rather, the receptacle is only intended to be in place during times when the user would like an increased level of discreteness and control over waste evacuation into the bag. Once the bag is full and/or the receptacle is no longer needed, the user simply detaches the receptacle from the flange whereupon the bag is allowed to fully unroll and is either left to completely fill or emptied and cleaned or replaced with a new bag, as desired.

In another embodiment, the bag is not used and waste collects directly into the receptacle which may be removed, emptied of waste, cleaned and reattached as desired. This provides an option to the user who may not want to use a bag or when their bag supply has run out.

BRIEF DESCRIPTION OF THE DRAWING

The above-mentioned and other features and advantages of this invention, and the manner of attaining them, will become apparent and be better understood by reference to the following description of the invention in conjunction with the accompanying drawing, wherein.

DETAILED DESCRIPTION OF A PREFERRED EMBODIMENT

Figure 1:
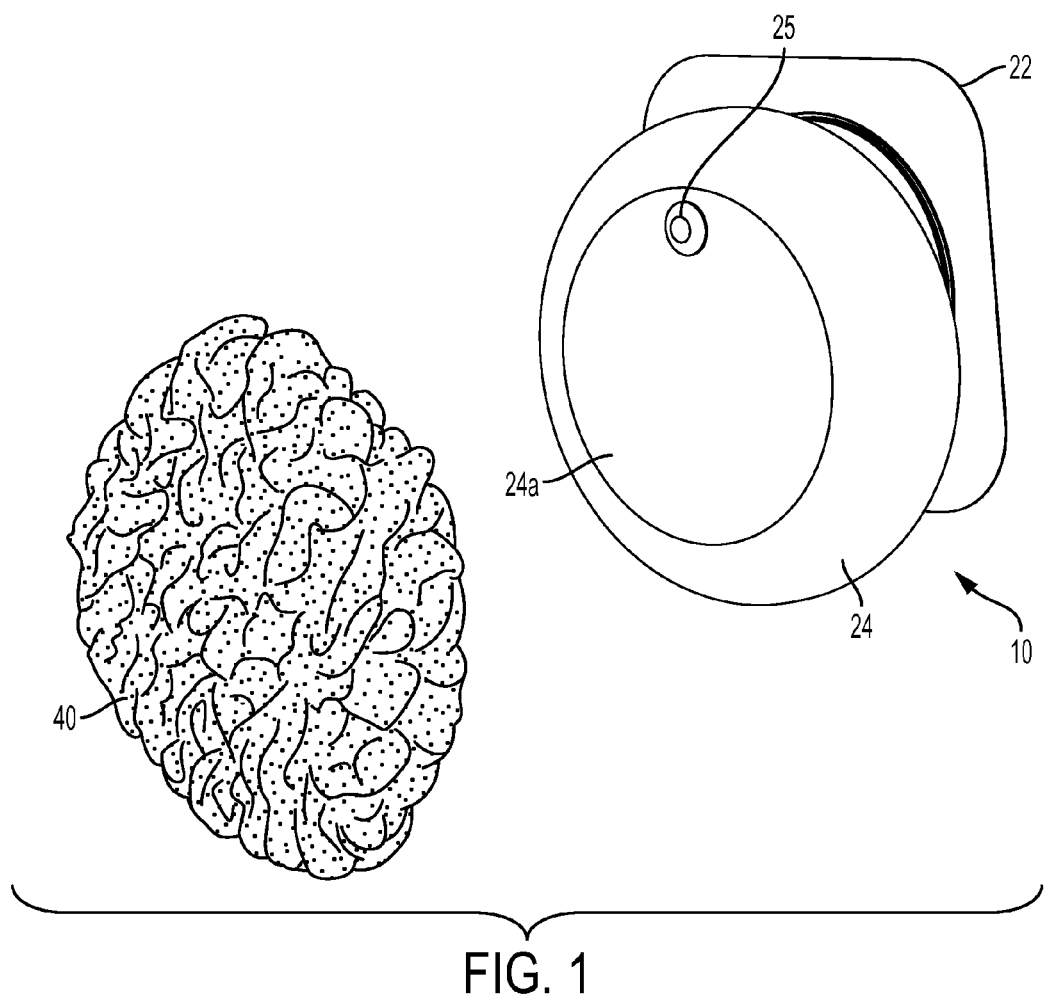
FIG. 1 is a perspective view of an embodiment of the inventive ostomy device.

Referring now to the drawing, there is seen in the various figures an ostomy appliance according to one embodiment of the invention indicated generally by the reference numeral 10. Ostomy appliance 10 includes a disc 12 having a central opening 14 for aligning with and positioning over a user's stoma (not shown). Disc 12 includes an adhesive surface 12a (see FIG. 2) for securing the disc about the stoma body tissue. Release paper (not shown) protects the adhesive surface 12a until time of use whereupon the user removes the release paper and adheres the disc surface 12a onto the stoma tissue with the opening of the stoma aligned with the disc opening 14.

A ring-shaped groove element 18 is attached to the perimeter of a first opening 20a of waste collection bag 20 and a ring-shaped flange 16 is affixed to disc 12 such that the bag may be releasably attached to the disc 12. Skirt 22 extends outwardly from ring-shaped flange 16 and includes an adhesive surface 22a for adhering to the user's body tissue which surrounds the stoma. A release paper (not shown) may protect the adhesive surface 22a until time of use whereupon the user removes the release paper and adheres the skirt 22 to the user's body while also adhering the disc adhesive surface 12a to the adjacent stoma tissue.

A cup-shaped receptacle 24 is provided for times when the user desires an increased level of discreteness. Receptacle 24 includes a bottom wall 24a and a side wall 24b terminating in a top perimeter edge 24c all defining an interior cavity 24d. The shape of the receptacle is such that side wall 24b forms an enlarged cavity portion 24e which extends downwardly in line with the length of the body toward the legs when attached to the user in the intended manner. This enlarged cavity portion 24e of the receptacle provides more portion within which the bag 20 may fit and begin to expand or unroll as the bag fills with the user's waste. This particular embodiment thus allows the receptacle to remain in place for a longer time than a receptacle that is more compact.

Figure 2:
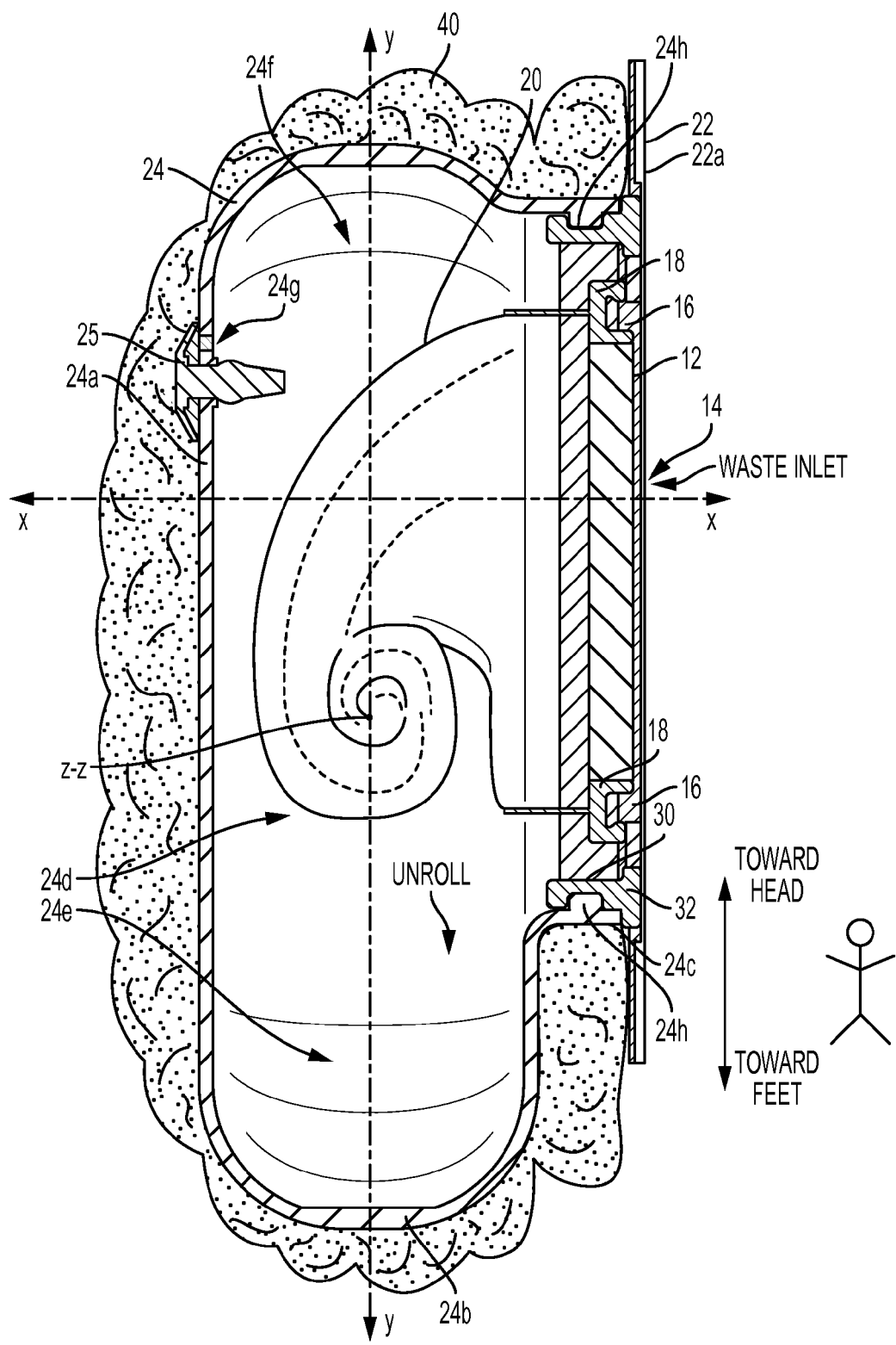
FIG. 2 is a side elevational view of the ostomy device of FIG. 1 showing the covering in position over the ostomy bag container with parts thereof shown in section.
Figure 3:
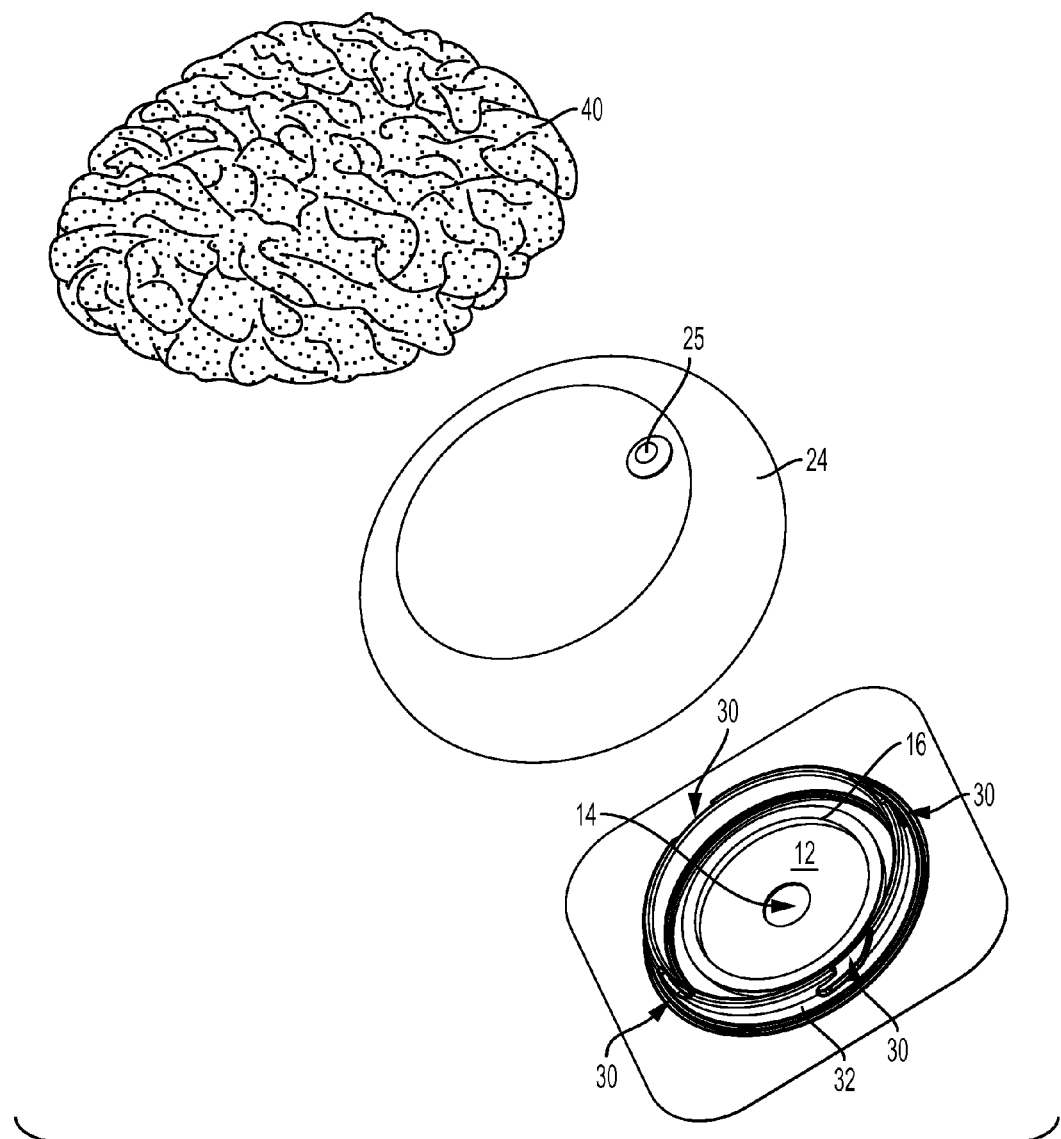
FIG. 3 is an exploded perspective view of the ostomy device absent the ostomy bag.

As seen best in FIG. 2, receptacle 24 is asymmetrically shaped about a horizontal axis x-x (relative to vertically standing user) extending through the center of opening 14 which is substantially concentrically placed over the user's stoma. The receptacle smaller cavity portion 24f is located above axis x-x and the stoma (toward user's head) and the enlarged cavity portion 24e is located below axis x-x and the stoma (toward the user's feet). This asymmetrical shape helps minimize the overall size of the receptacle in that the smaller cavity portion 24f is located above the stoma where waste does not usually get directed and the enlarged cavity portion 24e is located below the stoma where the waste and bag 20 are directed within the confines of the receptacle 24 due to gravity when the user is sitting upright or standing. In this regard, it is preferred that the user roll bag 20 up about an axis z-z which extends in the horizontal plane of and perpendicular to axes x-x and longitudinal axis y-y. As such, the bag 20 will be able to freely unroll in the direction of enlarged cavity portion 24e along and parallel to vertical longitudinal axis y-y as it is filled with waste.

Receptacle bottom wall 24a may include a small aperture 24g to allow gases from the stoma to vent therethrough. A vent plug 25 is provided which is operable to move between a normally closed aperture position and an open aperture position where a rise in gas pressure within receptacle 24 above a threshold pressure causes vent plug 25 to move to the open aperture position and thereby allowing the egress of gas from receptacle 24 through aperture 24g. Once the gas is released and the receptacle internal pressure lowers below the threshold pressure, the vent plug automatically sits back over and closes aperture 24g. This allows intermittent gas release rather than constant gas release and also prevents an unsafe pressure build-up within the receptacle.

Figure 6:
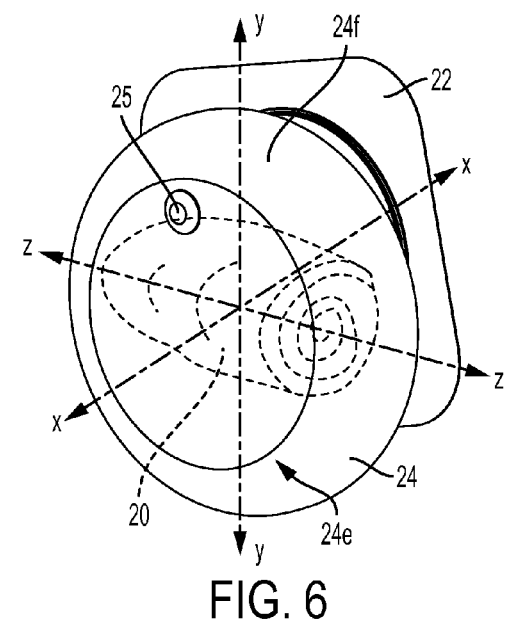
FIG. 6 is the view of FIG. 5 showing the ostomy bag container attached to the stoma flange with the folded bag showing in dotted lines inside the container.
Figure 5:
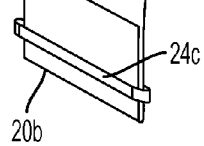
FIG. 5 is the view of FIG. 4 showing the ostomy bag in the folded condition and the ostomy bag container in portiond relation thereto.
Figure 5:
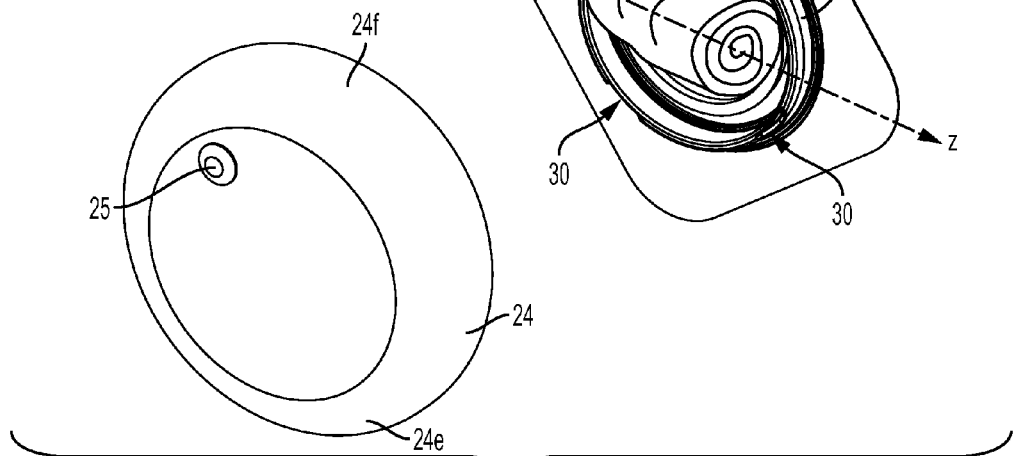

A receptacle attachment mechanism is provided for releasably securing receptacle 24 to the disc 12/flange 22 combination. The receptacle attachment mechanism may be provided in the form of a luer-type mechanism, for example. In this preferred embodiment, receptacle top perimeter edge 24c includes one or more tabs 24h which align with and may be screwed into a respective number of curved slots 30 formed in outer ring 32 affixed to disc 12 and thereby releasably securing receptacle 24 to ring 32. Prior to securing receptacle 24 to ring 32, the user rolls bag 20 up upon itself as shown in FIG. 5. Once receptacle 24 is attached to ring 32 in the manner described, bag 20 is located within receptacle 24 as shown in FIG. 6. Although a Luer-type mechanism is described and shown herein as comprising the receptacle attachment mechanism, it is of course understood that other attachment mechanisms which releasably secure receptacle 24 to ring 32 as desired.

Figure 4:
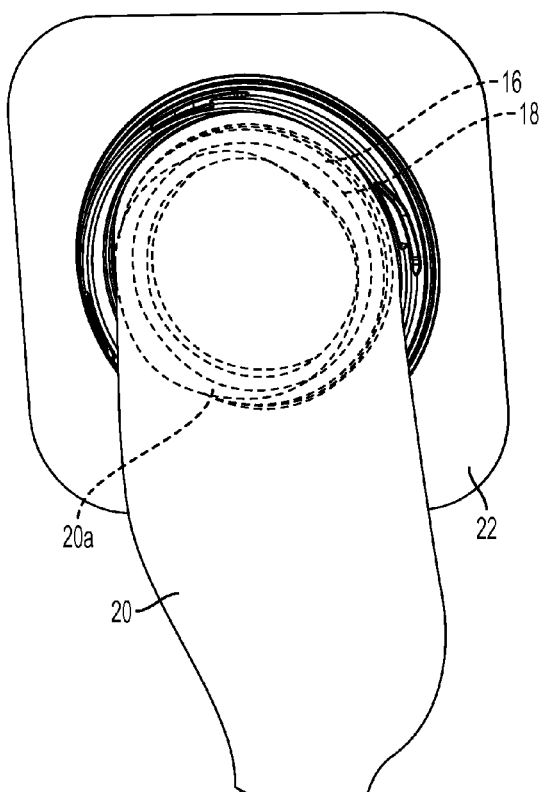
FIG. 4 is a perspective view showing the ostomy bag attached to the stoma flange with the bag in the unfolded position.

As described above, waste is free to enter bag 20 which may expand and unroll in the direction of enlarged cavity portion 24e. There is no positive pressure applied to the stoma during this time. The user may cover receptacle 24 with a fabric covering 40 having an elasticized opening 40a as seen in FIG. 2. In this manner, the user has increased his/her level of discreteness by confining their ostomy bag 20 to a relatively small receptacle 24 with a soft fabric covering. The user may thus engage in physical or other social activities with a greater sense of discreteness due to the control and concealment of the ostomy bag afforded by receptacle 24. When the user removes receptacle 24, bag 20 is free to fully unroll whereupon the user may empty waste from second bag opening 20b using resealable closure 20c (FIG. 4).

In another embodiment, the bag 20 is not used and waste collects directly into the receptacle 24 and will drop by gravity into enlarged cavity portion 24e. Receptacle 24 may thereafter be removed, emptied of waste, cleaned and reattached to disc 12 as desired. This provides an option to the user who may not want to use a bag or when their bag supply has run out.

Other embodiments of the invention may include features such as making receptacle 24 of a color changing material which is activated with increased heat. When waste is depositing into the bag or directly into the receptacle, the heat of the waste will heat the receptacle which in turn will change color, altering the user that it may be time to check their ostomy bag or receptacle or possible emptying or changing.

What is claimed is:

1. An ostomy device, comprising:
   a) a disc having an adhesive surface for applying to stoma tissue;
   b) a ring-shaped flange attached to said disc on the surface thereof opposite said adhesive surface;
   c) a bag having a first opening having a ring-shaped groove attached to the perimeter of said first opening, said ring-shaped groove releasably attachable to said ring-shaped flange to releasably attach said bag to said disc;
   d) a receptacle having a bottom wall, side wall and a top perimeter edge defining an interior cavity, said receptacle being asymmetrically shaped about a horizontal axis relative to a standing user, said asymmetrically shaped receptacle defining an enlarged cavity portion configured to hold a partially filled bag; and
   e) a receptacle releasable attachment mechanism configured to releasably attach said receptacle to said disc.

2. The ostomy device of claim 1 and further including an outer ring affixed to said disc and wherein said releasable attachment mechanism comprises one or more tabs formed on said receptacle top perimeter edge which may releasably attach to a like number of curved slots formed in said outer ring.

3. The ostomy device of claim 1 and further including an aperture in said receptacle bottom wall and a vent plug located adjacent said aperture and operable to move between a normally closed aperture position and an open aperture position where a rise in gas pressure within said receptacle above a threshold pressure causes said vent plug to move to said open aperture position and thereby allowing the egress of gas from said receptacle through said aperture.

4. An ostomy device configured to receive an ostomy bag, the ostomy device comprising:
   a) a disc having an adhesive surface for applying to stoma tissue;
   b) a ring-shaped flange attached to said disc on the surface thereof opposite said adhesive surface;
   c) a receptacle having a bottom wall, side wall and a top perimeter edge defining an interior cavity, said receptacle being asymmetrically shaped about a horizontal axis relative to a standing user, said asymmetrically shaped receptacle defining an enlarged cavity portion configured to hold a partially filled bag; and
   d) a receptacle releasable attachment mechanism configured to releasably attach said receptacle to said disc.

5. The ostomy device of claim 1 wherein said receptacle includes a color changing material which is activated by heat.

6. A method of using an ostomy appliance, said method comprising the steps of:
   a) providing an ostomy flange having a disc and an adhesive surface and a central opening;
   b) releasably attaching said disc to a user via said adhesive surface with said central opening located over the user's stoma;
   c) providing a receptacle having a bottom wall, side wall and a top perimeter edge defining an interior cavity, said receptacle being asymmetrically shaped about a horizontal axis relative to a standing user, said asymmetrically shaped receptacle defining an enlarged cavity portion; and
   d) removably attaching said receptacle to said disc with said open top perimeter positioned over said disc central opening and stoma.

7. The method of claim 6 and further comprising the step of:
   e) orienting said receptacle with said enlarged cavity portion extending in the direction of the user's feet when said receptacle is attached to said disc.

8. The method of claim 6 and further comprising the step of providing a bag having an open top and removably attaching said bag to said disc with said bag top opening positioned over said central opening and stoma.

9. The method of claim 7 and further comprising the step of rolling said bag up on itself about an axis which extends perpendicular to the longitudinal axis of said receptacle.

10. The method of claim 6 and further comprising the steps of:
    a) providing an outer ring with one or more curved slots formed therein and affixing said outer ring to said disc;
    b) providing one or more tabs on said receptacle top perimeter edge; and
    c) releasably attaching said receptacle to said outer ring with said one or more tabs engaging said one or more curved slots, respectively.

11. The ostomy device of claim 2 wherein each of said one or more tabs screws within a respective curved slot through a luer-type mechanism.

12. The ostomy device of claim 4 and further including an outer ring affixed to said disc and wherein said releasable attachment mechanism comprises one or more tabs formed on said receptacle top perimeter edge which may releasably attach to a like number of curved slots formed in said outer ring.

13. The ostomy device of claim 12 wherein each of said one or more tabs screws within a respective curved slot through a luer-type mechanism.

14. The method of claim 10 wherein each of said one or more tabs screws within a respective curved slot through a luer-type mechanism.

15. The method of claim 8 wherein the enlarged cavity portion of the receptacle is configured to hold a partially filled bag.

* * * * *